United States Patent

Fritsch et al.

[11] 4,128,593
[45] Dec. 5, 1978

[54] PRODUCTION AND RECOVERY OF PARA-CYMENE

[75] Inventors: Thomas R. Fritsch, Lombard; Mark C. Anderson, Palatine, both of Ill.

[73] Assignee: UOP Inc., Des Plaines, Ill.

[21] Appl. No.: 896,967

[22] Filed: Apr. 17, 1978

Related U.S. Application Data

[63] Continuation-in-part of Ser. No. 836,273, Sep. 26, 1977.

[51] Int. Cl.² ............................................. C07C 7/13
[52] U.S. Cl. ............................ 260/674 A; 208/143; 260/674 SA; 260/668 A
[58] Field of Search ............... 208/143; 260/674 SA, 260/674 A, 668 A

[56] References Cited

U.S. PATENT DOCUMENTS

| | | | |
|---|---|---|---|
| 2,585,899 | 2/1952 | Langlois | 260/668 A |
| 3,044,964 | 7/1962 | Morrell | 252/435 |
| 3,201,344 | 8/1965 | Broughton | 208/143 |
| 3,239,455 | 3/1966 | Lickus et al. | 208/212 |
| 3,285,982 | 11/1966 | Nixon | 260/666 |
| 3,636,121 | 1/1972 | Stine et al. | 260/674 SA |
| 3,636,180 | 1/1972 | Broughton | 260/668 A |
| 4,044,062 | 8/1977 | Korous et al. | 260/674 SA |

*Primary Examiner*—Delbert E. Gantz
*Assistant Examiner*—J. E. Spresser
*Attorney, Agent, or Firm*—James R. Hoatson, Jr.; Robert W. Erickson; William H. Page, II

[57] ABSTRACT

A mixture of cymene isomers, containing paracymene is subjected to adsorption-separation in contact with a crystalline aluminosilicate adsorbent which selectively retains para-cymene. Raffinate therefrom, being a para-cymene deficient mixture of cymene isomers, is isomerized to form additional para-cymene. Isomerization conditions employed to produce para-cymene, also effect formation of olefinic material. To prevent the adverse effect which olefins exhibit toward the efficiency and capacity of the zeolitic adsorbent, the isomerization effluent is subjected to hydrotreating at conditions which provide a liquid-phase operation and saturate olefins without saturation of the cymene isomers.

10 Claims, 1 Drawing Figure

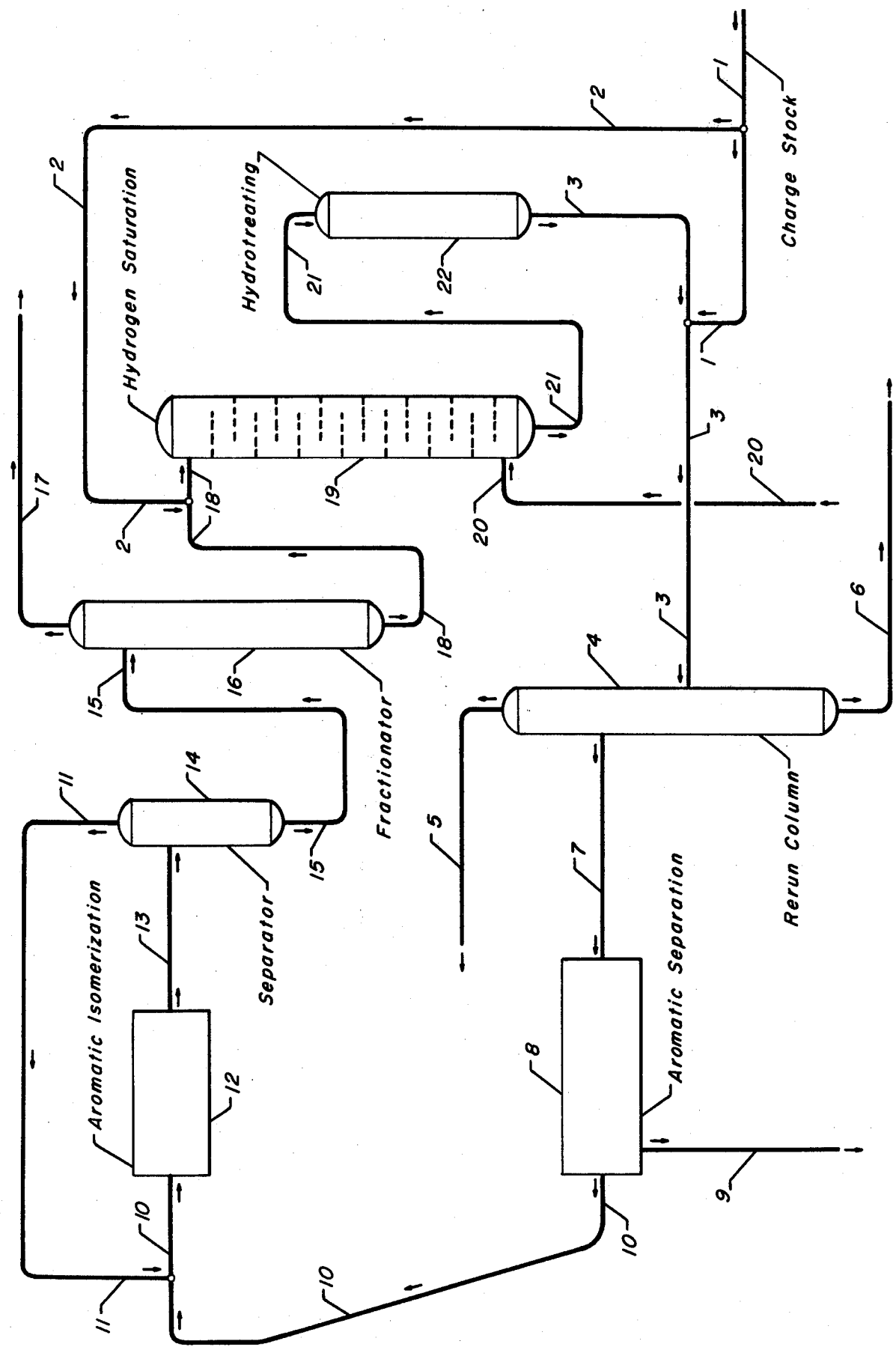

PRODUCTION AND RECOVERY OF PARA-CYMENE

RELATED APPLICATION

The present application is a continuation-in-part of our copending application, Ser. No. 836,273, filed Sept. 26, 1977, all the teachings of which are incorporated herein by way of specific reference thereto.

APPLICABILITY OF INVENTION

As herein described, the process encompassed by our inventive concept is directed toward the production and recovery of aromatic hydrocarbons. More specifically, the present invention is intended for utilization in the production of particular bi-alkyl substituted aromatic hydrocarbons having isomeric counterparts. One class of such compounds is the $C_8$-aromatics, ortho-xylene, metaxylene and para-xylene, a mixture of which generally includes ethylbenzene. Another class is the $C_{10}$-aromatics, ortho-cymene, meta-cymene and para-cymene. Of these isomeric hydrocarbons, the para isomers currently appear to be in the shortest supply and the greatest demand. Principal uses of para-xylene include the synthesis of terephthalic acid for ultimate production of synthetic resins and fibers, and in vitamin and other pharmaceutical synthesis. Para-cymene likewise has many commercial uses, the principal one of which is the production of para-cresol. Further description of our invention will be primarily directed toward the production and recovery of paracymene, without the intent to be so limited.

Regardless of the method by which para-cymene, or para-xylene is produced — e.g. catalytic condensation, isomerization — the product effluent generally comprises an equilibrium mixture of the isomers. The present invention is intended to be applicable to the recovery of the para-xylene, or para-cymene contained in such mixtures, and the production thereof via isomerization of the other components. The charge stock to the present process may be a substantially pure $C_8$-aromatic concentrate or mixture of cymene isomers, or a mixture thereof with other classes of hydrocarbons such as naphthenes, paraffins, etc. The $C_8$-aromatics are also obtained in the effluent from various petroleum conversion processes such as catalytic cracking, catalytic reforming, naphtha pyrolysis to produce ethylene, etc., while cymenes are typically produced by catalytic condensation of propylene with toluene. It is understood that the particular charge stock, or source of the feedstock is not a limitation upon the scope of our invention.

Briefly, a mixture of cymene isomers is subjected to adsorption-separation in contact with a crystalline aluminosilicate adsorbent which selectively retains therein the para-cymene which is removed and recovered therefrom through the use of a suitable desorbent. The rejected cymene isomers are isomerized in contact with an acid-acting catalytic composite comprising a phosphorus component. We have found that at the conditions necessary to effect isomerization reactions to form additional paracymene, olefinic hydrocarbons are produced in relatively minor quantities. Those skilled in the art of adsorption-separation via contact with crystalline aluminosilicate molecular sieves are well aware of the detrimental effects exhibited by even minor amounts of olefinic hydrocarbons upon the capacity and efficiency of the zeolitic molecular sieve to adsorb the desired component of the mixture. As hereinafter indicated, this awareness is evidenced by prior art processes which utilize a hydrotreating zone in the pretreatment of a fresh feed charge stock; however, such prior art pretreatment is effected with the intent to saturate olefins and aromatics, as well as reducing both sulfur and nitrogen concentrations. In accordance with our invention, the hydrotreating technique constitutes a low-severity, liquid-phase operation effected at conditions which saturate the olefins without substantial saturation of aromatic hydrocarbons.

OBJECTS AND EMBODIMENTS

A principal object of our invention is to provide a more efficient process for the production and recovery of para-cymene. A corollary objective is to enhance the efficiency and capacity of a crystalline aluminosilicate adsorbent employed in the adsorption-separation of para-cymene from its isomers.

More specifically, it is an object to improve a combination aromatic isomerization/adsorption-separation process for the production and recovery of para-cymene from a mixture of cymene isomers.

In one embodiment, therefore, our invention directs itself toward a process for the production and recovery of para-cymene from a mixture of cymene isomers, which process comprises the sequential steps of: (a) contacting said mixture with a crystalline aluminosilicate adsorbent, in an adsorption-separation zone, at conditions selected to effect the selective retention therein of para-cymene; (b) withdrawing a para-cymene deficient raffinate stream from said adsorption-separation zone and contacting said adsorbent with a desorbent to effect removal and recovery of para-cymene therefrom; (c) introducing raffinate stream into an aromatic isomerization reaction zone maintained at isomerization conditions which convert cymene isomers into para-cymene and which effect the production of olefinic hydrocarbons; (d) hydrotreating the resulting isomerization reaction zone effluent, in a hydrotreating zone, at hydrotreating conditions selected to (i) provide a liquid-phase operation and (ii) saturate said olefinic hydrocarbons without substantial saturation of cymene isomers; and, (e) introducing at least a portion of the resulting olefin-free reaction zone effluent into said adsorption-separation zone to recover additional para-cymene.

In a preferred embodiment, the isomerization of the ortho- and meta-cymene concentrate, to produce additional para-cymene, is effected utilizing a phosphorus-containing catalyst. Suitable catalysts are those commonly known in the prior art as "solid phosphoric acid" catalysts; these are described below.

Other objects and embodiments will become evident, to those possessing the requisite degree of skill in the appropriate art, from the following more detailed discussion. In one such other embodiment, the cymene isomer fresh feed mixture is combined with the olefin-free hydrotreating effluent, and introduced therewith into the molecular sieve adsorption-separation zone. Another embodiment involves introducing the cymene isomer charge stock into the hydrotreating zone in admixture with the isomerization zone effluent.

CITATION OF RELEVANT PRIOR ART

As hereinbefore stated, our inventive concept encompasses the known combination process of (1) producing para-xylene and para-cymene via the catalytic isomerization of $C_8$-aromatic and $C_{10}$-aromatic hydrocarbon mixtures, respectively, and, (2) the recovery thereof by way of selective adsorptive-separation utilizing a zeolitic, crystalline aluminosilicate molecular sieve. In essence, a liquid-phase, catalytic hydrotreating reaction zone is interposed between the isomerization section and the adsorptive-separation section. This serves to eliminate olefinic hydrocarbons, formed during the aromatic isomerization reaction, via hydrogenation to paraffinic counterparts which are innocuous with respect to the selected crystalline aluminosilicate adsorbent employed in the adsorptive-separation section. Through this technique, the capacity and efficiency of the zeolitic molecular sieve is significantly improved.

It is recognized and acknowledged that many illustrations of aromatic isomerization processing techniques are to be found in the prior art; likewise, zeolitic molecular sieve adsorption/separation has been shown to be applicable to many classes of hydrocarbons. Since the process encompassed by the present invention involves isomerization of bi-alkyl substituted aromatic hydrocarbons in combination with molecular sieve adsorption/-separation to recover the desired para-isomer, which combination has an intermediate hydrotreating zone, it is believed that the most relevant prior art will be directed toward (1) combinations of isomerization and zeolitic adsorption/separation, particularly as directed toward cymene isomers, (2) hydrotreating in combination with the separation of classes of hydrocarbons by way of crystalline aluminosilicate adsorption and, (3) particular catalytic composites for use in the isomerization of the ortho- and meta-isomers to para-isomers. Copies of the prior art hereinafter delineated accompany this application.

U.S. Pat. No. 3,636,121 (Cl. 260-674A), issued Jan. 18, 1972, directs itself toward a dual adsorption and isomerization process utilizing first and second molecular sieve adsorption zones. The first adsorption zone effects separation of the fresh feed stream (a $C_8$-aromatic concentrate) into (1) a para-xylene/ethylbenzene concentrate and, (2) an ortho-xylene/meta-xylene concentrate. The latter stream is subjected to isomerization, to produce additional para-xylene/ethylbenzene, the effluent from which is passed into the first adsorption zone. The para-xylene/ethylbenzene concentrate therefrom is introduced into the second molecular sieve separation zone from which the para-xylene and ethylbenzene are recovered as individual streams. Nowhere is there recognition of the deleterious effects of olefinic hydrocarbons, produced in minor quantities in the isomerization reaction zone, upon the efficiency and capacity of the zeolitic molecular sieve adsorbent. Furthermore, the teachings do not contemplate a low severity, liquid-phase hydrotreatment for the purpose of rendering these olefinic hydrocarbons innocuous.

U.S. Pat. No. 3,636,180 (Cl. 260-668A), issued Jan. 18, 1972, is similar to the foregoing. However, provisions are made to the overall process flow to permit introduction of the aromatic feed stream to the isomerization zone, to a fractionation zone, or to the adsorption-separation zone; fractionation facilities are also provided to afford recovery of any specific one of the three isomers. In Column 5, Lines 39-42, it is stated that the process is utilizable for recovering a particular isomer from $C_9$-aromatic and $C_{10}$-aromatic hydrocarbon feedstocks.

U.S. Pat. No. 3,201,344 (Cl. 208-143), issued Aug. 17, 1965, is specifically directed toward a combination process for refining hydrocarbon lubricating oils. Adsorption-separation is effected utilizing a 13X or 10X molecular sieve to reject, as the raffinate stream, branched chain hydrocarbons, polynuclear cyclics and polyalkyl-substituted cyclics which are the less desirable components of lubricating oils. Prior to adsorptive-separation, the lube oil stock is subjected to hydrogenation to saturate the aromatic and olefinic hydrocarbons (Column 4, Lines 14-30) to provide the more desirable paraffinic and naphthenic components of the lubricating oil. The hydrogenative pretreatment is apparently conducted in a liquid-phase operation (Column 7, Lines 17-49). Since the charge stock, being an unrefined lube oil consisting of hydrocarbons in the $C_{18}$ to $C_{25}$ range, as distinguished from naphtha boiling range hydrocarbons, liquid-phase hydrogenation constitutes a judicious operating technique. Noteworthy, however, is the absence (1) of such hydrogenation technique in an isomerization/adsorption combination process and, more significantly, (2) liquid-phase conditions which prevent the saturation of aromatic nuclei.

U.S. Pat. No. 3,239,455 (Cl. 208-212), issued Mar. 8, 1966, is primarily concerned with the recovery of normal aliphatic hydrocarbons boiling in the kerosene boiling range for ultimate use in detergent manufacture (Column 1, Lines 14-45). Hydrogenation of the fresh feed charge stock is effected to eliminate nitrogenous and sulfurous compounds, and to saturate olefinic and aromatic hydrocarbons (Column 2, Lines 1-45). The hydrogenation pretreatment is effected in liquid phase (Column 6, Lines 43-54 and Column 12, Lines 20-25). As above indicated, the hydrotreating reaction employed in our combination aromatic isomerization/adsorption-separation process is effected at conditions which preclude aromatic hydrocarbon saturation.

U.S. Pat. No. 4,044,062 (Cl. 260-674SA), issued Aug. 23, 1977, is directed toward the adsorptive-separation of a para isomer from hydrocarbon charge stock containing alkyl-substituted aromatics having more than eight carbon atoms per molecule. The separation process utilizes type X, or type Y structured zeolites, and is particularly directed toward para-diethyl-benzene and para-cymene, both of which contain ten carbon atoms per molecule. Zeolitic adsorbents contain exchanged cations from the group of potassium, rubidium, cesium, barium, copper, silver, lithium, sodium, beryllium, magnesium, calcium, strontium, cadmium, cobalt, nickel, manganese and zinc. Particularly preferred are combinations of two such cations (Column 3, Lines 18-25).

U.S. Pat. No. 2,585,899 (Cl. 260-668), issued Feb. 12, 1952, directs itself toward the isomerization of alkylated aromatic hydrocarbons, and particularly dialkyl benzenes having from one to four carbon atoms in each alkyl group. Phosphoric acid catalyst is employed in order to minimize side reactions such as disproportionation and cracking of alkyl side chains which results in gaseous hydrocarbon production. Such advantageous results are afforded in view of the fact that the desired isomerization reactions can be effected at lower catalyst bed temperatures. The preferred catalyst is solid phosphoric acid which comprises orthophosphoric acid on a suitable porous carrier material such as kieselguhr.

Solid phosphoric acid catalysts are employed in other petroleum type reactions including alkylation and polymerization, both of which may be categorized as catalytic condensation reactions. Such catalysts are also suitable for utilization herein. One such solid phosphoric acid catalyst is described in U.S. Pat. No. 3,044,964 (Cl 252-435), issued July 17, 1962, as is its method of preparation. Similarly, U.S. Pat. No.

3,285,982 (Cl. 260-666), issued Nov. 15, 1966, directs itself to isomerization of hydrocarbons, including alkylaromatic hydrocarbons (Column 3, Lines 5–14). Desired reactions are effected in contact with an anhydrous catalyst containing both phosphoric acid and a halogen, which catalyst is intended to inhibit decomposition reactions.

SUMMARY OF INVENTION

As hereinbefore set forth, the process encompassed by our inventive concept is adaptable to the production and recovery of aromatic hydrocarbons from a mixture thereof with other aromatic hydrocarbons. In particular, our invention is intended for (1) the production and recovery of para-xylene from a mixture of other $C_8$-aromatic hydrocarbons and, (2) the production and recovery of para-cymene from a mixture of other cymene isomers. In the interest of brevity and simplicity, the following discussion will be limited to para-cymene recovery and production. The charge stock to the present combination process is generally a substantially pure mixture of cymene isomers. Regardless, it is understood that the present process does not require the fresh feed charge stock to be a concentrated aromatic stream.

Considering cymene isomer concentrates, which will contain minor quantities of $C_9$-hydrocarbons (including aromatics) as well as $C_{11}$-plus hydrocarbons, they will generally be obtained from a hydrocarbonaceous stream which has previously been hydrotreated. For example, commonly practiced techniques dictate the hydrorefining of naphtha boiling range material, for olefinic saturation and the destructive removal of sulfurous and nitrogenous compounds, prior to its use as the feedstock for catalytic reforming. The aromatic concentrate recovered from the reformed product effluent will, therefore, be substantially free from these contaminating influences. Where such an aromatic concentrate is virtually immediately charged to the present process, it may be directly introduced into the adsorption-separation zone. However, we have also found that the feedstock requires hydrotreating where it has been exposed to air prior to its use herein. In this situation, the feedstock is admixed with the effluent from the aromatic isomerization zone and introduced therewith into the hydrotreating zone.

Hydrotreating is effected after the aromatic isomerization reaction zone and prior to the adsorption-separation zone. Briefly, the cymene isomer charge stock is introduced into a so-called rerun or stripper column from which lower boiling components are removed as an overhead stream and $C_{11}$-plus material is withdrawn as a bottoms stream. The cymene isomers are separately recovered as a heart-cut and introduced into the adsorption-separation zone, contacting therein a crystalline aluminosilicate from the group of type X and type Y zeolites. Para-cymene is selectively retained within the sieves, and removed and recovered therefrom through the use of a suitable desorbent such as toluene. A para-cymene deficient concentrate of meta-cymene, ortho-cymene and methyl propylbenzene is withdrawn as a raffinate stream and introduced into an aromatic hydrocarbon isomerization reaction zone. Conversion to the para-cymene isomer is effected in contact with an acidic catalytic composite preferably comprising phosphorus or a phosphoric acid component. The isomerized product effluent is subjected to separation to provide a hydrogen recycle stream and to remove the greater proportion of $C_9$-aromatics and lower boiling material.

Details of both the zeolitic adsorption-separation zone and the aromatic isomerization reaction zone are separately discussed hereinbelow.

Although the isomerization product effluent has been separated to provide the hydrogen-rich recycle stream (containing normally gaseous hydrocarbons) and to remove $C_9$-aromatics and lower boiling material, the normally liquid cymene isomer mixture will have dissolved therein an otherwise insignificant quantity of olefinic hydrocarbons. However, since the intent is to introduce this material into the molecular sieve adsorption-separation zone for recovery of the additional para-cymene, the minor amount of olefins must be removed in order to preserve the integrity of the crystalline aluminosilicate adsorbent. Accomplishment is effected via low-severity, liquid-phase hydrogenation which saturates the olefins without destroying the character of aromatic nuclei.

The cymene mixture is introduced into the upper section of a hydrogen saturation zone which is maintained at a pressure in the range of about 10 to about 500 psig., preferably from 10 to about 50 psig., and a temperature of about 100° F. to about 400° F. Precise conditions are selected to absorb a slight excess of hydrogen above that required to saturate the olefinic hydrocarbons. Hydrogen is most conveniently introduced into the saturation zone on pressure control — as the pressure decreases in the saturation vessel, the hydrogen rate is increased. The cymene mixture, containing sufficient dissolved hydrogen, is passed into the hydrotreating zone which preferably has disposed therein a substantially non-acidic catalytic composite comprising a Group VIII noble metal component. Suitable noble metal components are ruthenium, osmium, rhodium, iridium, platinum, palladium and mixtures thereof. Preferably, these are composited with an alumina carrier material. Hydrotreating is carried out at low-severity conditions which results in a liquid-phase operation with respect to the isomeric cymenes. These include temperatures of 100° F. to 400° F. and pressures from about 10 to about 500 psig. Through the use of the noble metal/alumina composite, the olefins will be saturated while the aromatic hydrocarbons will pass through virtually unscathed. The use of the term "non-acidic" is intended to allude to the fact that intentional steps to provide an acid function — e.g. incorporation of a silica or halogen component — in the catalyst, are not taken. Noble metals, especially platinum and palladium, as well as the alumina carrier material, possess sufficient natural acidity to effect hydrogenation reactions at a low severity operation. Concentrations of the noble metal component will be within the range of about 0.1% to about 1.5% by weight, calculated on the basis of the elemental metal. Relatively high liquid hourly space velocities of from about 2.5 to about 10.0 also contribute to the low severity operation by which there is no substantial aromatic hydrogenation.

The olefin-free cymene concentrate from the hydrotreating zone is admixed with olefin-free fresh feed charge stock and introduced therewith into the rerun column, from which the cymene isomer feed to the adsorption-separation zone is recovered as a sidecut from the upper part of the column. Where analyses indicate that the stored charge stock contains oxygenated and/or olefinic hydrocarbons, the same will be admixed with the effluent from the isomerization reaction zone and introduced therewith into the hydrogen saturation chamber.

ADSORPTION-SEPARATION

In describing the aromatic adsorption-separation section of the present combination process, particularly as directed toward selective para-xylene adsorption, it is understood that the precise manner by which the separation is effected forms no essential feature of our invention. Recognized is the fact that the prior art, whether published literature, or issued patents, abounds with various aspects of molecular sieve technology, and especially as applied to the adsorptive separation of various hydrocarbon mixtures. In such prior art, the terms "zeolite", "crystalline aluminosilicate" and "molecular sieve" are employed synonymously to allude to various structures of crystalline alumina and silica having pores in which one or more components of a given hydrocarbon mixture are selectively sorbed and retained within the pores, while one or more other components are rejected. Zeolitic adsorbents fall into a variety of classifications, generally determined by pore size and structure, depending upon the character of the component to be retained as well as the character of those components to be rejected. Thus, molecular sieves having a pore diameter of about five angstrom units are widely utilized to separate normal paraffins (sorbed and retained) from isoparaffins (rejected). Although the adsorption-separation may be effective using multiple fixed-bed zeolitic zones in swing-bed fashion, as illustrated in U.S. Pat. No. 2,920,037 (Cl. 208-310), issued Jan. 5, 1960, the more recent sophisticated simulated moving bed technique, as illustrated in U.S. Pat. No. 2,985,589 (Cl. 210-34), issued May 23, 1961, is preferred. These simulated moving bed processes utilize a multi-port rotary valve which may be of the type shown in U.S. Pat. No. 3,040,777 (Cl. 137-625.15), issued June 26, 1962.

With respect to the separation and recovery of para-cymene, suitable adsorbents are the type X and type Y crystalline aluminosilicate zeolites. General details of the composition and manufacturing technique of these may be had upon reference to U.S. Pat. No. 4,044,062 (Cl. 260-674SA), issued Aug. 23, 1977. These molecular sieve zeolites contain exchangeable cationic sites which, by way of ion-exchange, will be prepared to contain one or more metal cations from the group of lithium, potassium, beryllium, magnesium, calcium, strontium, barium, nickel, copper, silver, manganese and cadmium. Generally, the cations of the metals from Groups I-A and II-A are preferred; a type X or type Y zeolite containing both potassium and barium is especially preferred.

Both liquid-phase and vapor-phase adsorptions may be utilized in this section of the present process, with the former being preferred. Liquid phase requires somewhat lower temperatures which enchance the selectivity of the zeolite with respect to para-cymene. Typical adsorption-separation conditions include temperatures of from about 100° F. to about 400° F. and pressures in the range of from atmospheric to about 500 psig. Suitable desorbents constitute those materials readily separable from the $C_{10}$-aromatic components — i.e., having a different boiling range such that fractional distillation is feasible. Suitable desorbents include benzene, toluene, ethers, alcohols and ketones. Desorption conditions include the same ranges of temperature and pressure employed in the adsorption step. Additional details of the use of crystalline aluminosilicates in the adsorption-separation and recovery of alkylaromatics, may be obtained by reference to the following U.S. Pat. Nos. 3,558,732 (Cl. 260–674), issued Jan. 26, 1971; 3,626,020 (Cl. 260–674SA), issued Dec. 7, 1971; 3,663,638 (Cl. 260-674SA), issued May 16, 1972; 3,665,046 (Cl. 260-674SA), issued May 23, 1972; and, 3,696,107 (Cl. 260-674SA).

AROMATIC ISOMERIZATION

As previously stated in the discussion of the aromatic hydrocarbon separation section via zeolitic adsorption, it is acknowledged that the published literature is replete with illustrations of aromatic isomerization processes. The raffinate stream recovered from the separation zone contains principally ortho-cymene and meta-cymene. The specific technique employed to isomerize at least a portion of this mixture to produce additional para-cymene isomer is not a feature essential to the present invention. Preferably, the raffinate stream is contacted with an acidic catalytic composite comprising a phosphorus or phosphoric acid component. Other known hydrocarbon isomerization catalyst may be utilized, although not necessarily with equivalent results. For example, isomerization may be carried out with a catalytic composite comprising a Group VIII noble metal component, in a hydrogen atmosphere. Suitable catalysts contain at least one metal from the group of ruthenium, rhodium, palladium, osmium, iridium, platinum and mixtures thereof, with platinum and/or palladium being particularly advantageous. As stated in U.S. Pat. No. 3,078,318 (CL. 260-668), issued Feb. 19, 1963, the catalytically active metallic component are composited with an alumina carrier material, containing about 0.1% to about 8.0% by weight of combined chlorine and/or fluorine; the noble metal concentration will be in the range of about 0.01% to about 1.0% by weight, calculated as the elemental metal.

With this type of catalytic composite, the paracymene deficient raffinate will be isomerized to produce additional para-cymene at operating conditions including temperatures of from 700° F. to about 1100° F., preferably 750° F. to 1000° F., and pressures in the range of about atmospheric to about 1,500 psig., preferably 100 to 700 psig. The reactions are effected in the presence of hydrogen in an amount of about 1.0 to about 10.0 moles per mole of hydrocarbon charge. Raffinate components will be charged to the isomerization reaction zone at a weight hourly space velocity of from 0.5 to about 10.0, preferably in the range of about 1.0 to about 5.0. Particular operating conditions will be dependent upon the particular mixture of $C_{10}$-hydrocarbons in the feedstock; however, combinations of higher pressures and lower temperatures should be avoided to assure substantially no aromatic hydrogenation.

Additional details of suitable aromatic isomerization techniques may be had upon reference to the following U.S. Pat. Nos. 3,409,685 (Cl. 260-668), issued Nov. 5, 1968, wherein isomerization is effected with a Group VIII metal component on an alumina matrix having crystalline aluminosilicate suspended therein, and in the presence of a sulfur-containing promoter; 3,409,686 (Cl. 260-668), issued Nov. 5, 1968, wherein the catalyst is platinum on an alumina carrier having finely-divided zeolitic material suspended therein; and, 3,637,881 (Cl. 260-668A), issued Jan. 25, 1972, which teaches the suppression of transalkylation through the addition of a basic nitrogen-containing compound to the isomerization reaction zone.

Various Friedel-Crafts metal halides may also be employed in the aromatic isomerization reaction zone. Examples of such metal halides include aluminum chloride, aluminum bromide, antimony pentachloride, beryllium chloride, germanium tetrachloride, ferric chloride, ferric bromide, gallium tetrabromide, titanium tetrachloride, zinc bromide, zinc chloride and zirconium chloride, etc. Of these, aluminum chloride and/or aluminum fluoride are preferred. This is due to the ease of catalyst preparation and, more importantly, these Friedel-Crafts metal halides offer high activity for isomerization at decreased operating severity. Thus, the isomerization zone can function at lower temperatures of from 600° F. to about 900° F. and lower pressure of from atmospheric to about 600 psig. These catalysts are also advantageous in that they afford increased throughput at the same level of operating severity, thus further decreasing the incidence of decomposition reactions with respect to the alkyl side chains.

As hereinabove stated, the preferred catalyst is one containing a phosphorus or phosphoric acid component. Such catalytic composites afford still lower operating severities, especially temperatures in the range of about 400° F. to about 850° F., and thus further decrease the occurrence of decomposition reactions. Pressures of from atmospheric to about 500 psig. may be maintained in the isomerization reaction zone. As stated in U.S. Pat. No. 2,585,899 (delineated in the previous discussion of prior art), a hydrogen diluent in the charge stream tends to suppress the undesired side reactions while simultaneously inhibiting carbon and/or coke formation and deposition. Orthophosphoric acid combined with a porous carrier such as activated carbon of kieselguhr, including minor quantities of metallic modifiers, constitutes one of the preferred catalysts for utilization herein.

U.S. Pat. No. 3,285,982 (also previously discussed as part of the prior art) offers an improved solid phosphoric acid type catalyst; in this instance, a halogen component chemically combined with the phosphoric acid portion of the composite. Satisfactory supports, or carrier materials, are characterized as being refractory inorganic oxides including various aluminas, silica, magnesia, zirconia, thoria and mixtures thereof. Phosphoric acid comprises from 8.0% to 80.0% by weight of the catalytic composite, and preferably from about 10.0% to about 50.0%. The latter range is significantly less than those found in prior solid phosphoric acid catalysts. From about 1.0% to about 25.0% by weight of the catalyst will consist of the halogen component.

Use of solid phosphoric acid catalysts further lowers the operating severity, particularly in regard to temperature which can be in the lower range of about 400° F. to about 850° F. for the $C_{10}$-aromatic feed stream. Therefore, although not critical, the use of such catalysts is preferred herein. Regardless of the selected catalytic composite, it is understood that the method used in its manufacturing procedure forms no essential feature of our invention.

BRIEF DESCRIPTION OF DRAWING

Various embodiments of the combination process encompassed by our inventive concept are presented in the accompanying drawing. These are presented by way of a simplified schematic flow diagram in which miscellaneous appurtenances such as pumps and compressors, heaters and coolers, condensers, heat-exchangers and heat-recovery circuits, start-up lines, valving and similar hardware have been omitted. These are not essential to an understanding of the process, and the utilization thereof, to modify the illustration, is well within the purview of one possessing the requisite skill in the petroleum processing field of endeavor. Certainly the resulting modification will not be beyond the scope and spirit of the appended claims.

DETAILED DESCRIPTION OF DRAWING

The charge stock, being a cymene isomer concentrate recovered from an alkylation, or catalytic condensation process charging propylene and toluene, is introduced into the process by way of conduit 1. This is admixed with a previously hydrotreated effluent in line 3, the mixture continuing therethrough into rerun column 4. This column serves to remove minor amounts of nonanes and lower-boiling hydrocarbons, as well as normally vaporous material as an overhead stream in line 5. Normally liquid hydrocarbons containing eleven or more carbon atoms per molecule are concentrated and recovered by way of conduit 6. The $C_{10}$-aromatic concentrate is recovered from column 4 as a heart-cut in line 7, and is introduced thereby into aromatic separation zone 8.

Aromatic separation zone 8 contains an adsorbent of type X structured zeolitic material having about 1.3% sodium, 3.5% potassium and 18.6% barium, on a weight basis. Both adsorption and desorption operations are effected at liquid-phase conditions of 350° F. and about 200 psig. Para-cymene is adsorbed by the molecular sieves, and the material not selectively retained is removed by way of line 10. The adsorbent is contacted with a desorbent — e.g. toluene — to displace the selectively adsorbed para-cymene which is recovered via conduit 9. The para-cymene deficient stream in line 10 is introduced thereby into aromatic isomerization zone 12 in admixture with a hydrogen-rich vaporous phase in line 11. Employed herein is a catalytic composite of alumina containing about 45.0% by weight of phosphoric acid and about 6.5% by weight of chlorine. Operating conditions include a pressure of about 150 psig., a temperature of about 700° F., a liquid hourly space velocity of about 3.0 and hydrogen to hydrocarbon mole ratio of about 6.0:1.0. The isomerized effluent is passed into high-pressure separator 14 by way of line 13 at a temperature of about 90° F. Excess hydrogen-rich vapors, not recycled to isomerization zone 12 are vented under pressure control (not illustrated).

Normally liquid hydrocarbons, containing dissolved normally vaporous material and olefinic hydrocarbons are withdrawn from separator 14 through line 15, and introduced thereby into fractionator 16. Nonane and lower boiling hydrocarbons, including vaporous material, are recovered through line 17, while the $C_{10}$-aromatic concentrate is recovered by way of conduit 18. As above stated, where the fresh feed in line 1 contains olefinic hydrocarbons, or other zeolite contaminating influences, it will be mixed with the aromatic concentrate in line 18 and introduced therewith into hydrogen saturation zone 19.

Hydrogen saturation zone 19 contains a plurality of trays or other devices creating intimate mixing of the hydrocarbons in line 18 and the hydrogen in line 20. With respect to the latter, a portion thereof may be supplied from the excess hydrogen-rich stream not recycled to aromatic isomerization zone 12 via line 11. Saturation with hydrogen is effected at a temperature of about 360° F. and a pressure of about 35 psig. The absorbed hydrogen-containing $C_{10}$-aromatic concentrate is withdrawn through line 21 and introduced into hydrotreating zone 22. Therein the mixture contacts a non-acidic catalytic composite of about 0.375% by weight of platinum combined with an alumina carrier material. The liquid hourly space velocity is about 3.0, while the temperature and pressure are essentially the same as those employed in the aromatic separation zone — 350° F. and 200 psig. Olefin-free $C_{10}$-aromatics are withdrawn via line 3 and introduced into rerun column 4 in admixture with the fresh feed charge stock in line 1.

The foregoing specification, particularly when read in conjunction with the accompanying drawing, clearly indicates the method by which the present combination process is effected.

We claim as our invention:

1. A process for the production and recovery of para-cymene from a mixture of cymene isomers which process comprises the sequential steps of:
   (a) contacting said mixture with a crystalline aluminosilicate adsorbent, in an adsorption-separation zone, at conditions selected to effect the selective retention therein of para-cymene;
   (b) withdrawing a para-cymene deficient raffinate stream from said adsorption-separation zone and contacting said adsorbent with a desorbent to effect removal and recovery of para-cymene therefrom;
   (c) introducing said raffinate stream into an aromatic isomerization reaction zone maintained at isomerization conditions which convert cymene isomers into para-cymene and which effect the production of olefinic hydrocarbons;
   (d) hydrotreating the resulting isomerization reaction zone effluent, in a hydrotreating zone, at hydrotreating conditions selected to (i) provide a liquid-phase operation and (ii) saturate said olefinic hydrocarbons without substantial saturation of cymene isomers; and,
   (e) introducing at least a portion of the resulting olefin-free reaction zone effluent into said adsorption-separation zone to recover additional para-cymene.

2. The process of claim 1 further characterized in that said cymene isomer mixture is combined with said olefin-free effluent and introduced therewith into said adsorption-separation zone.

3. The process of claim 1 further characterized in that said cymene isomer mixture is combined with said isomerization reaction zone effluent and introduced therewith into said hydrotreating zone.

4. The process of claim 1 further characterized in that said $C_{10}$-aromatic hydrocarbon mixture comprises para-cymene and at least one aromatic hydrocarbon from the group of meta-cymene and ortho-cymene.

5. The process of claim 1 further characterized in that said hydrotreating conditions include a temperature in the range of about 100° F. to about 400° F. and a pressure from about 10 to about 500 psig.

6. The process of claim 5 further characterized in that said hydrotreating conditions include a pressure in the range of about 10 to about 50 psig.

7. The process of claim 1 further characterized in that said adsorbent is selected from the group consisting of type X and type Y structured zeolites.

8. The process of claim 1 further characterized in that said desorbent comprises toluene.

9. The process of claim 1 further characterized in that said aromatic isomerization reaction zone has disposed therein a catalytic composite comprising phosphorous.

10. The process of claim 1 further characterized in that said hydrotreating reaction zone has disposed therein a substantially non-acidic catalytic composite comprising a Group VIII metallic component.

* * * * *